US012478764B2

(12) United States Patent
Ninni

(10) Patent No.: US 12,478,764 B2
(45) Date of Patent: Nov. 25, 2025

(54) MEDICAL APPARATUS AND METHOD OF USE THEREOF

(71) Applicant: Canon U.S.A., Inc., Melville, NY (US)

(72) Inventor: Brian Ninni, Woburn, MA (US)

(73) Assignee: CANON U.S.A., INC., Melville, NY (US)

( * ) Notice: Subject to any disclaimer, the term of this patent is extended or adjusted under 35 U.S.C. 154(b) by 264 days.

(21) Appl. No.: 17/373,437

(22) Filed: Jul. 12, 2021

(65) Prior Publication Data

US 2022/0016394 A1 Jan. 20, 2022

Related U.S. Application Data

(60) Provisional application No. 63/052,795, filed on Jul. 16, 2020.

(51) Int. Cl.
*A61M 25/01* (2006.01)

(52) U.S. Cl.
CPC .... *A61M 25/0147* (2013.01); *A61M 25/0108* (2013.01); *A61M 2025/015* (2013.01)

(58) Field of Classification Search
CPC .......... A61M 25/0147; A61M 25/0108; A61M 2025/015
See application file for complete search history.

(56) References Cited

U.S. PATENT DOCUMENTS 5,195,968 A * 3/1993 Lundquist .......... A61M 25/0147 604/95.04
5,383,852 A * 1/1995 Stevens-Wright .......... A61M 25/0136 604/95.04
5,438,975 A * 8/1995 Miyagi .......... A61B 1/00071 600/141
5,545,200 A * 8/1996 West .......... A61M 25/0136 606/29
6,033,378 A * 3/2000 Lundquist .......... A61M 25/0147 604/95.01
6,837,849 B2 * 1/2005 Ogura .......... A61B 1/0055 600/146
8,182,417 B2 * 5/2012 Danitz .......... A61B 1/0055 606/1
10,512,392 B2 * 12/2019 Gurusamy .......... A61B 1/008
2002/0068868 A1 * 6/2002 Thompson .......... A61M 25/0144 604/95.01
2002/0082585 A1 * 6/2002 Carroll .......... A61M 25/0105 604/95.04

(Continued)

FOREIGN PATENT DOCUMENTS

JP 2015002858 A 1/2015
JP 2018171701 A 11/2018

(Continued)

*Primary Examiner* — Alexander J Orkin
(74) *Attorney, Agent, or Firm* — Canon U.S.A., Inc. IP Division

(57) ABSTRACT

An articulated medical device having a hollow core, capable of large degrees of maneuverability through small spaces of a patient to reach a target with minimal invasiveness, and once the medical device has reached the target, allowing for finite movement of the distal end of the medical device to hone in on one or more targets or areas of interest, without having to move the remainder of the medical device.

15 Claims, 5 Drawing Sheets

(56) References Cited

U.S. PATENT DOCUMENTS

| | | | | | |
|---|---|---|---|---|---|
| 2002/0165571 | A1* | 11/2002 | Hebert | A61B 17/12136 | 606/192 |
| 2003/0018318 | A1* | 1/2003 | Melsky | A61M 25/0144 | 604/526 |
| 2004/0102719 | A1* | 5/2004 | Keith | A61M 25/0147 | 600/585 |
| 2004/0122360 | A1* | 6/2004 | Waldhauser | A61M 25/005 | 264/234 |
| 2004/0186378 | A1* | 9/2004 | Gesswein | A61M 25/0152 | 604/528 |
| 2005/0107667 | A1* | 5/2005 | Danitz | A61B 34/70 | 600/139 |
| 2005/0273084 | A1* | 12/2005 | Hinman | A61B 1/0051 | 606/1 |
| 2005/0288626 | A1* | 12/2005 | Koerner | A61M 25/0147 | 604/95.04 |
| 2005/0288656 | A1* | 12/2005 | Koerner | A61M 25/0043 | 604/95.04 |
| 2006/0004323 | A1* | 1/2006 | Chang | A61F 2/186 | 604/28 |
| 2007/0239170 | A1* | 10/2007 | Brock | A61B 17/0483 | 606/1 |
| 2009/0171274 | A1* | 7/2009 | Harlev | A61B 5/6859 | 604/95.04 |
| 2010/0168666 | A1* | 7/2010 | Tegg | A61M 25/0147 | 604/95.04 |
| 2010/0228191 | A1* | 9/2010 | Alvarez | A61M 25/0105 | 604/95.01 |
| 2010/0280449 | A1* | 11/2010 | Alvarez | A61B 34/71 | 606/1 |
| 2011/0092956 | A1* | 4/2011 | Soer | A61B 1/00156 | 604/528 |
| 2011/0152880 | A1* | 6/2011 | Alvarez | A61M 25/0147 | 606/130 |
| 2012/0232563 | A1* | 9/2012 | Williams | A61M 25/0108 | 606/129 |
| 2013/0096497 | A1* | 4/2013 | Duindam | A61M 25/0133 | 604/95.01 |
| 2013/0102960 | A1* | 4/2013 | Miyoshi | A61M 25/0136 | 604/95.04 |
| 2013/0197306 | A1* | 8/2013 | Armand | A61M 25/0138 | 604/95.04 |
| 2014/0187949 | A1 | 7/2014 | Zhao et al. | | |
| 2014/0276933 | A1* | 9/2014 | Hart | A61M 25/0147 | 606/130 |
| 2014/0309661 | A1* | 10/2014 | Sheps | A61F 2/2427 | 606/130 |
| 2015/0250983 | A1* | 9/2015 | Ruijters | A61B 6/12 | 604/95.04 |
| 2016/0183841 | A1 | 6/2016 | Duindam et al. | | |
| 2017/0095234 | A1* | 4/2017 | Prisco | A61B 34/20 | |
| 2018/0126119 | A1* | 5/2018 | McNiven | A61M 25/0136 | |
| 2019/0076093 | A1* | 3/2019 | Saroha | A61B 5/027 | |
| 2019/0105468 | A1* | 4/2019 | Kato | A61M 25/0113 | |

FOREIGN PATENT DOCUMENTS

| | | | |
|---|---|---|---|
| JP | 2019093119 | A | 6/2019 |
| JP | 2019122491 | A | 7/2019 |

* cited by examiner

MEDICAL APPARATUS AND METHOD OF USE THEREOF

CROSS REFERENCE TO RELATED PATENT APPLICATIONS

This application claims priority from U.S. Provisional Patent Application No. 63/052,795, filed on Jul. 16, 2020, in the United States Patent and Trademark Office, the disclosure of which is incorporated herein in its entirety by reference.

FIELD OF THE DISCLOSURE

The present disclosure relates generally to apparatus and methods for medical application. More particularly, the subject disclosure is directed to an articulated medical device having a hollow chamber, wherein the device is capable of maneuvering within a patient, and allowing a medical tool to be guided through the hollow chamber for medical procedures, including endoscopes, cameras, and catheters.

BACKGROUND OF THE DISCLOSURE

Bendable medical instruments such as endoscopic surgical instruments and catheters are well known and continue to gain acceptance in the medical field. The bendable medical instrument generally includes a flexible body commonly referred to as sleeves or sheaths. One or more tool channels extend along (typically inside) the flexible body to allow access to a target located at a distal end of the body.

The instrument is intended to provide flexible access within a patient, with at least one curve or more leading to the intended target, while retaining torsional and longitudinal rigidity so that a physician can control the tool located at the distal end of the medical instrument by maneuvering the proximal end of the instrument.

To enhance maneuverability of the distal end of the instrument, robotized instruments that control distal portions have emerged. In those robotized instruments, to create curves locally at the distal portion by robotics, different techniques have been disclosed.

However, as much as advancements in localizing the area of interest in a patient, in three-dimensional space, have improved, there remain a good number of miscalculations and/or shifting of instruments and/or a patient, leading to incorrect targeting.

By way of example, United States patent publication number 2014/0187949, relates to navigating a catheter to a target and adjusting the deployment position based on a number of factors, including probability of hitting the target. It also includes multiple deployment locations. United States patent publication number 2016/0183841, also discloses methods of presenting navigation and targeting information to the user using a steerable catheter, including the reachable area and deployment location. However, neither of these references present multiple bending section solutions.

Existing catheter designs provide for the ability to translate the tip position in space without affecting the orientation. Single section bending only allows for orientation to change, and the position can only be changed by physically repositioning the catheter. As such, being able to adjust the position without affecting the orientation or catheter position is desirable for a number of reasons. For instance, it allows for a more finite adjustment of the target location at larger distances or it could allow for more surface area coverage depending on the shape of the lesion, as well as providing a true range of target which may be adjusted without having to advance the catheter or change the existing shape/position of the catheter.

SUMMARY

Thus, to address such exemplary needs in the industry, the presently disclosed device teaches a medical apparatus comprising a bendable body having a first bending section and a second bending section, with the first bending section in a position distal to the second bending section; a first control wire connected to a distal end of the first bending section; a second control wire connected to a distal end of the second bending section; at least two lumens in the bendable body extending the length of the bendable body through both the first bending section and second bending section; wherein the first bending section comprises: at least two guide rings disposed in the bendable body and spaced a distance from one another to create a cavity; and a wall extending the length of the first bending section and configured to encapsulate the at least two guide rings, wherein the wall comprises a resilient outer lining and a resilient inner lining for encapsulating the at least two rings, wherein the first bending section is configured for manipulation after the second bending section has been advanced to reach the target.

In various embodiments, the manipulation of the first bending section is accomplished while the second bending section is stationary.

In yet additional embodiments, the manipulation of the first bending section is selected from the group consisting of rotation, fore and aft travel, panning, translation, movement in two axes, and movement in three axis.

In is further contemplated that the at least two guide rings are attached to at least a portion of the wall.

In addition, the inner lining defines a hollow chamber.

In yet another embodiment, the apparatus further comprising an actuator attached to a proximal end of the at least one control wire, wherein the actuator is configured to actuate the control wire.

The apparatus may further comprise a support wire slideably situated in the at least one lumen.

In additional embodiments, the at least two lumens extend through the at least two guide rings. Furthermore, the control wire and lumen comprise of a radio opaque material.

In yet additional embodiments, the apparatus further comprising a controller for calculating the path of the bendable body.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
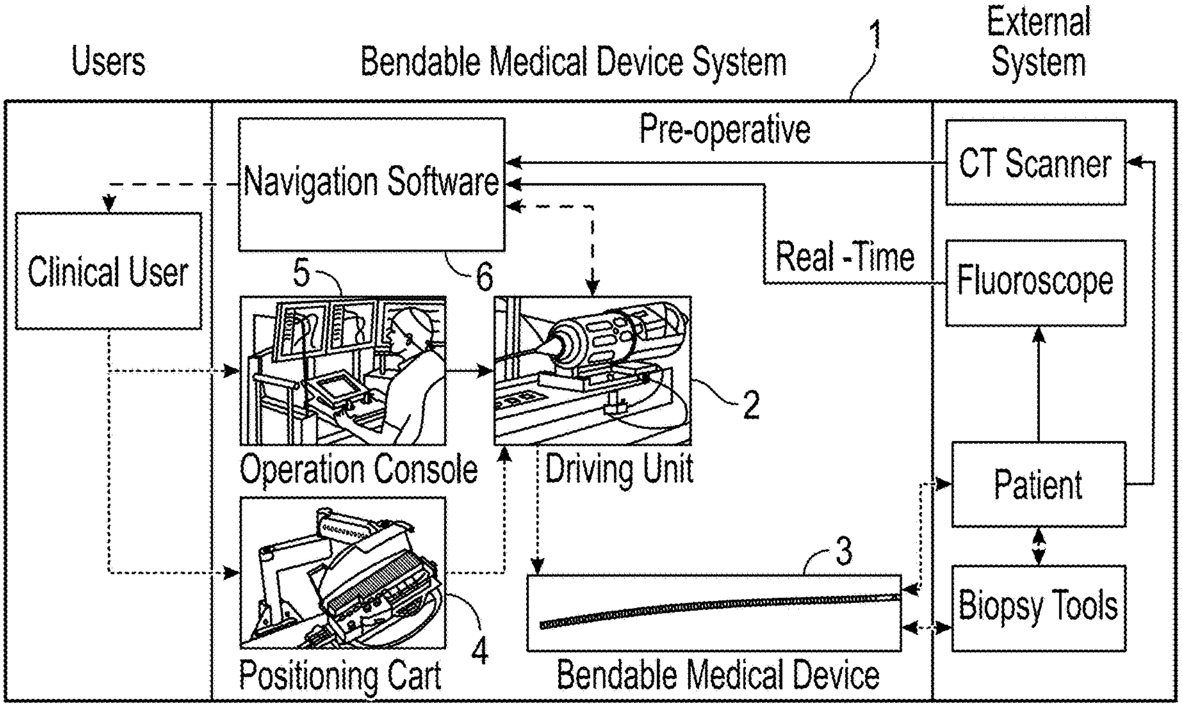
FIG. 1 is a block diagram of an exemplary bendable medical device incorporating various ancillary components, according to one or more embodiment of the subject apparatus, method or system.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

FIG. 1 is a system block diagram of an exemplary bendable medical device system 1 incorporating various ancillary components intended to amass a complete medical system. The bendable medical device system 1 comprises a driving unit 2, a bendable medical device 3, a positioning cart 4, an operation console 5 and navigation software 6. The exemplary bendable medical device system 1 is capable of interacting with external system component and clinical users to facilitate use in a patient.

The navigation software 6 and the driving unit 2 are communicatively-coupled via a bus to transmit/receive data between each other. Moreover, the navigation software 6 is connected and may communicate with a CT scanner, a fluoroscope and an image server (not in Figure), which are ancillary components of the bendable medical device system 1. The image server may include, but is not limited to, a DICOM™ server connected to a medical imaging device including but not limited to a CT and/or MRI scanner and a fluoroscope. The navigation software 6 processes data provided by the driving unit 2 and data provided by images stored on the image server, and/or images from the CT scanner and the fluoroscope in order to display images onto the image display.

The images from the CT scanner may be pre-operatively provided to navigation software 6. With navigation software, a clinical user creates an anatomical computer model from the images. In this particular embodiment, the anatomy is that of a lung with associated airways. From the chest images of the CT scanner, the clinical user can segment the lung airways for clinical treatments, such as biopsy. After generating the lung airway map, the user can also create plan to access the lesion for the biopsy. The plan includes the airways to insert and maneuver the bendable medical device 3 leading to the intended target, which in this example is a lesion.

The driving unit 2 comprises actuators and a control circuitry. The control circuitry is communicatively-coupled with operation console 5. The driving unit 2 is connected to the bendable medical device 3 so that the actuators in the driving unit 2 operate the bendable medical device 3. Therefore, a clinical user can control the bendable medical device 3 via the driving unit 2. The driving unit 2 is also physically connected to a positioning cart 4. The positioning cart 4 includes a positioning arm, and locates the driving unit 2 and the bendable medical device 3 in the intended position with respect to the target/patient. The clinical user can insert, maneuver and retreat the bendable medical device 3 to perform medical procedures, here a biopsy in the lungs of the patient.

The bendable medical device 3 can be navigated to the lesion in the airways based on the plan by the clinical user's operation. The bendable medical device 3 includes a hollow chamber for various tools (e.g. a biopsy tool). The bendable medical device 3 can guide the tool to the lesion of the patient. In one example, the clinical user can take a biopsy sample from the lesion with a biopsy tool.

Figure 2:
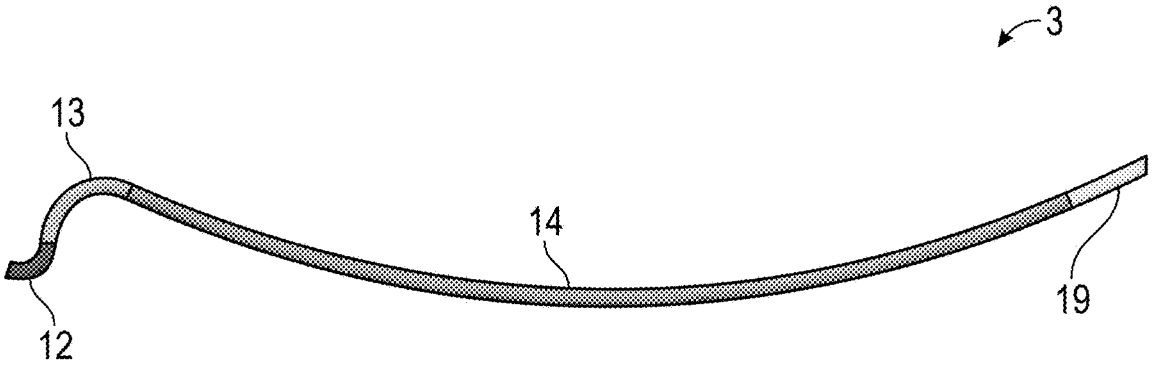
FIG. 2 depicts a perspective view of an exemplary bendable medical device, according to one or more embodiment of the subject apparatus, method or system.

FIG. 2 is a schematic drawing to explain the bendable segments of the bendable medical device 3. The bendable medical device 3 comprises a proximal part 19 and three bendable segments, which are the first, second, and third bendable segments 12, 13, 14, respectively. The bendable segments 12, 13, 14, can independently bend and can form a shape with three independent curvatures, as seen in FIGS. 4 and 5.

Figure 3A:
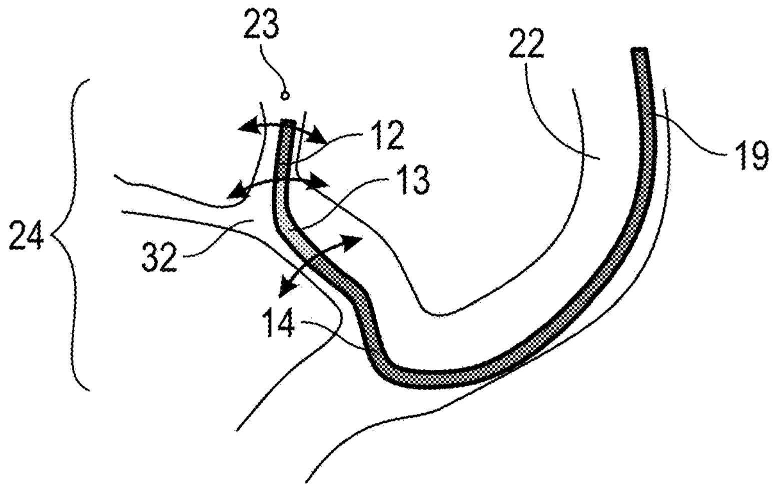
FIG. 3*a* provides a cut-away view of an exemplary bendable medical device inserted into a patient, according to one or more embodiment of the subject apparatus, method or system.

FIG. 3*a* provides a cut-away view of an exemplary bendable medical device 3 inserted into a patient, specifically, the peri-bronchial area of a patient's lungs, which is a lateral area surrounding the airways. This area is a known challenge to target as identified in literature, and the prior art, due to the limited distal dexterity of the conventional catheter. To reach the lesion through airways 22 in the navigation stage, the first and the second bendable segments 12, 13, respectively, navigate the bendable medical device 3 through the bifurcation point 32. The first bendable segment 12 can adjust the shape/orientation to the daughter branch while the second bendable segment 13 can adjust the shape/ orientation to the parent branch in the bifurcation point 32, as the bendable medical device 3 advances through the bifurcation point 32. Once the first and the second bendable segments 12 and 13 pass the bifurcation point 32, those segments may act as guides for the rest of the bendable medical device 3, so that the insertion force from the proximal end of the bendable medical device 3 can be effectively transformed into the insertion force for a distal part of the bendable medical device 3 without serious prolapsing of the distal section. Once the distal end 24 of the bendable medical device 3 reaches the vicinity of the lesion 23, the bendable medical device 3 would direct the distal end 24 to the lesion 23, which locates the lateral area around the airway, by bending the first and the second bendable segments 12 and 13, respectively. Since the airway doesn't directly connect with the lesion 23, this is one of the more difficult configurations for a conventional catheter.

With the first, the second and the third bendable segments 12, 13 and 14, respectively, the bendable medical device 3 can orient the distal end 24 without moving the proximal part 19 that goes through all bifurcations to this lesion 23. By using the three-dimensional bending capability of the first and the second bendable segments 12 and 13, the bendable medical device 3 can perform unique maneuvers to enhance capability of the peri-bronchial targeting. Therefore, the bendable medical device 3 can provide improved access to the intended lesion 23 through tortuous pathways. Also, the bendable medical device 3 can have different flexibility along the axial direction without increasing the size or number of the jointing points.

Figure 3B:
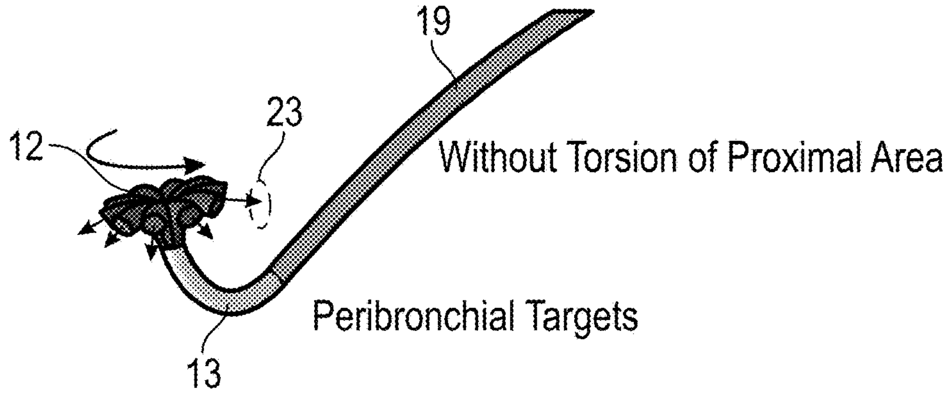
FIG. 3*b* provides a perspective view of an exemplary bendable medical device depicting various orientation options, according to one or more embodiment of the subject apparatus, method or system.
Figure 3C:
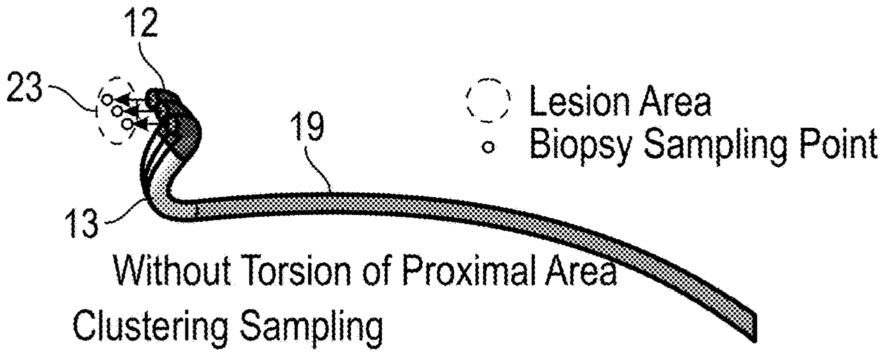
FIG. 3*c* depicts a perspective view of an exemplary bendable medical device depicting various orientation options, according to one or more embodiment of the subject apparatus, method or system.

FIG. 3*a* provides a cut-away view of an exemplary bendable medical device 3 inserted into a patient, wherein FIGS. 3*b* and 3*c* provide perspective views of an exemplary bendable medical device 3 depicting various orientation/maneuvering options.

FIGS. 3*a*, 3*b* and 3*c* are schematic drawings to explain the navigation and targeting of a lesion in peri-bronchial area of a patient's lungs, which is a lateral area surrounding the airways. This area is a known challenge to target as identified in literature, and the prior art, due to the limited distal dexterity of the conventional catheter. To reach the lesion through airways 22 in the navigation stage, the first and the second bendable segments 12, 13, respectively, navigate the bendable medical device 3 through the bifurcation point 32. The first bendable segment 12 can adjust the shape/orientation to the daughter branch while the second bendable segment 13 can adjust the shape/orientation to the parent branch in the bifurcation point 32, as the bendable medical device 3 advances through the bifurcation point 32. Once the first and the second bendable segments 12 and 13 pass the bifurcation point 32, those segments may act as guides for the rest of the bendable medical device 3, so that the insertion force from the proximal end of the single catheter can be effectively transformed into the insertion force for a distal part of the single catheter without serious prolapsing of the distal section. Once the distal end 24 of the bendable medical device 3 reaches the vicinity of the lesion, the bendable medical device 3 would direct the distal end 24 to the lesion 23, which locates the lateral area around the airway, by bending the first and the second bendable segments 12 and 13, respectively. Since the airway doesn't directly connect with the lesion 23, this is one of the more difficult configurations for a conventional catheter.

With the first, the second and the third bendable segments 12, 13 and 14, respectively, the bendable medical device 3 can orient the distal end 24 without moving the proximal part 19 that goes through all bifurcations to this lesion. By using the three-dimensional bending capability of the first and the second bendable segments 12 and 13, the bendable medical device 3 can perform unique maneuvers to enhance capability of the peri-bronchial targeting (FIGS. 3*b*, 3*c*). Furthermore, by incorporating different positions for the anchors 21 between the first 9, second 10 and third ii control wires along the axial direction of the bendable body 7, the bendable body 7 can function as different bending segments along the axial direction, because the control wires 9, 10, 11, are mapped to the different position of the bendable body 7. Therefore, the bendable medical device 3 can provide improved access to the intended lesion through tortuous pathways. Also, the bendable medical device 3 can have different flexibility along the axial direction without increasing the size or number of the jointing points.

In a first maneuver in an omni-directional orientation (FIG. 3*b*), the first bendable segment 12 can effectively rotate without rotating any part of the bendable medical device 3. This maneuver is beneficial to determine the orientation of the distal end to the lesion 23 since this motion isn't affected by the physical interaction of the proximal part of the catheter to the anatomy, as well as not affecting the position of lesion 23, while physically mapping the orientation of the distal end 24. Moreover, with the second bendable segment 13, the bendable medical device 3 can perform this omni-directional orientation after going through the final bifurcation point to reach the lesion 23. During this rotation, the bendable medical device 3 can rotate the bending plane of only the first bendable segment 12 without moving the second and the third bendable segments 13 and 14.

The second maneuver is a clustering sampling, as provided in FIG. 3*c*. The first bendable segment 12 can dislocate the position of the distal end while keeping the orientation of the distal end. With this maneuver, the distal end can access the different positons in the lesion 23. The advantage of this maneuver is to access different positions in the lesion 23, or to perform fine adjustment of the position of distal end. The bendable medical device 3 can dislocate the distal end with the identical orientation. Therefore, the resolution (and accuracy/precision) of the positioning is directly related to the dislocation of the distal end.

Figure 4A:
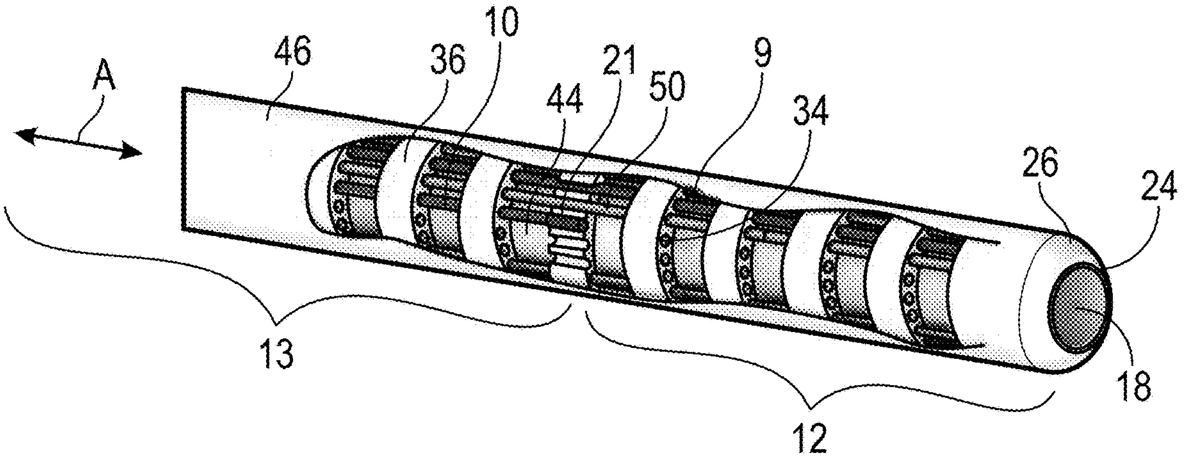
FIG. 4*a* provides a cut-away perspective view of an exemplary bendable medical device, according to one or more embodiment of the subject apparatus, method or system.
Figure 4B:
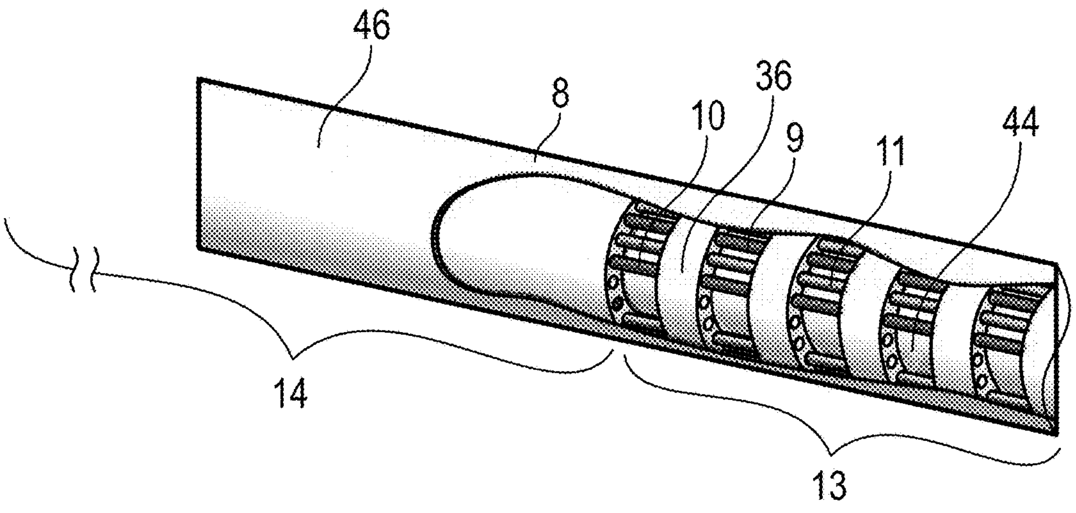
FIG. 4*b* is a close-up cut-away perspective view of an exemplary bendable medical device, according to one or more embodiment of the subject apparatus, method or system.
Figure 5:
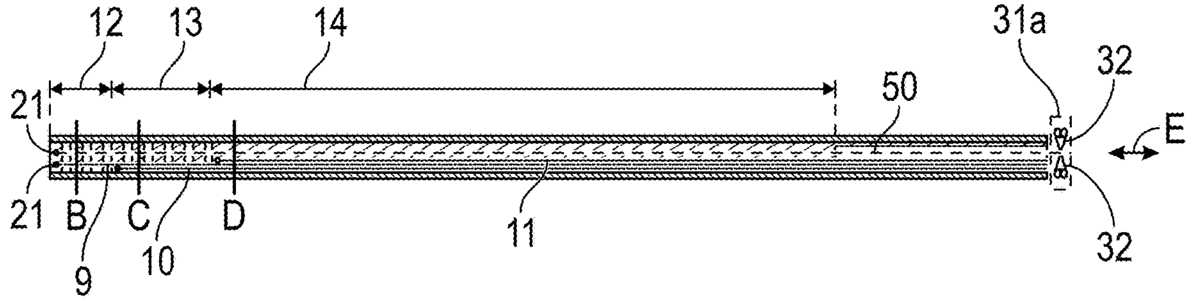
FIG. 5 provides a side perspective view of an exemplary bendable medical device, according to one or more embodiment of the subject apparatus, method or system.

As depicted in FIGS. 4*a* and 4*b*, the bendable medical device 3 includes a bendable body 7, wherein at least a portion of the structure of the bendable body 7 comprises multiple wire guides 36, wherein the wire guides 36 are configured a distance apart from one another and do not contact one another. The wire guides 36 are held in place by the cylindrical wall 8, which comprises an inner lining 44 and an outer lining 46, which provides bendable support to the bendably body 7 while retaining the wire guides 36 in a constant position along the axial direction of the bendable body 7. The inner lining 44 creates an inner diameter 40 and the outer lining 46 creates an outer diameter 42, wherein the inner diameter 40 establishes a tool channel 18. The edge of the bendable body 7 may be rounded by an atraumatic tip 26, to further diminish any harm to the internal elements of a patient as the bendable body 7 is advanced.

The adjacent guide rings 36, are attached to the inner lining 44 and outer lining 46, with cavities 30, created between the adjacent guide rings 36, distributed along the longitudinal direction of the bendable body 7. When bendable body is bent, the cavities 30 create evenly distributed wrinkles 60 (see FIG. 8*a*) in both the inner lining 44 and outer lining 46. Therefore, the cavities 30 avoid fatal kinking which may crush the tool channel 18 even when the bending sections 12 and 13 include thin total wall thickness.

In the depicted embodiment, the first bendable segment 12 and second bendable segment 13 incorporate wire guides 36 to provide structural support to the bendable medical device 3, while the third bendable segment 14 incorporates a more conventional wall without any gaps. The subject innovation is not limited to this particular embodiment, and the use of wire guides 36 may be used in any section, in whole or partially, within the bendable body and/or bendable medical device 3. For instance, the wire guides 36 may be used in the first bendable segment 12 and third bendable segment 14, with the second bendable segment 13 incorporating wire guides in limited part.

Each wire guide 36 contains at least two lumens 34, for slideable housing of the control wires 9-11, and is further configured to accept an anchor 21, which is displaced at the end of the control wires 9-11, to be embedded into the wire guides 36. In FIG. 4*a*, control wire 10 depicts the anchor 21, configured at the distal end of the second bendable segment 13. The space between adjacent wire guides 36, in cooperation with the resilient inner lining 44 and outer lining 46, allows the bendable body 7 to achieve a greater range of bending motion due to the open space between the wire guides 36, without kinking.

The tool channel 18 is configured to extend the length of the bendable body 7, wherein the proximal part 19 of the bendable body 7 provides access to clinical users for inserting/retreating a medical tool. For example, a clinical user can insert and retrieve a biopsy tool trough the tool channel 18 to the distal end 24 of the bendable medical device 3.

Figure 6A:
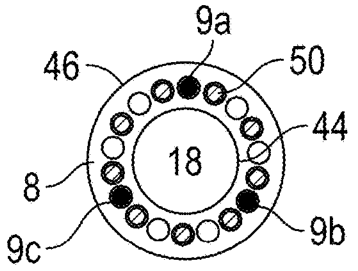
FIG. 6*a* depicts a cross-sectional view of an exemplary bendable medical device, according to one or more embodiment of the subject apparatus, method or system.
Figure 6B:
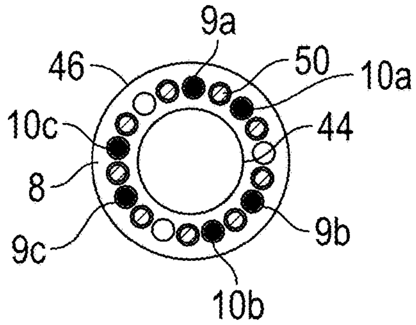
FIG. 6*b* provides a cross-sectional view of an exemplary bendable medical device, according to one or more embodiment of the subject apparatus, method or system.
Figure 6C:
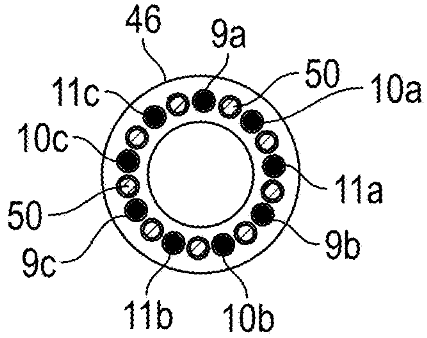
FIG. 6*c* depicts a cross-sectional view of an exemplary bendable medical device, according to one or more embodiment of the subject apparatus, method or system.

FIGS. 6*a* through 6*c* depict cross-sectional views of exemplary bendable medical devices shown in FIG. 5, according to one or more embodiment of the subject apparatus, method or system. FIG. 6*a* depict the cross-section view at the "B" line in FIG. 5, while FIG. 6*b* depicts the cross-sectional view at the "C" line, while FIG. 6*c* shows us the cross-sectional view at the "D" line of FIG. 5.

The bendable body 7 includes a set of first control wires 9*a*, 9*b*, 9*c*, a set of second control wires 10*a*, 10*b*, 10*c*, and a set of third control wires 11*a*, 11*b*, 11*c* housed in the wall 8, wherein each of the set of control wires 9, 10 and 11, corresponds to the first, second and third bendable segments 12, 13 and 14, respectively. The cylindrical wall 8 is formed by an inner lining 44 and an outer lining 46 which are congruent and combine with one another at the distal end 24 to encapsulate and form the wall 8. The wall 8 provides bendable support to the bendably body 7 while retaining the wire guides 36 in a constant position along the axial direction of the bendable body 7. The inner lining 44 creates the inner diameter 40 of the wall and establishes the tool channel 18, while the outer lining 46 creates the outer diameter 42 of the bendable body 7.

The wall 8 houses each of the control wires 9*a*-11*c* in corresponding lumens 34, configured along the longitudinal direction of the bendable body 7. The lumens 34 allow for slideable movement of the control wires 9*a*-11*c* along an axial direction of the bendable body 7. The control wires 9*a*-11*c* are terminated at the distal end of each bendable segments 12, 13 and 14, and form three groups with three wires each (a, b, c). The first control wires 9*a*, 9*b*, 9*c* are terminated at the distal end of the first bendable segment 12 with anchors 21, and are configured apart from each other by approximately 120 degrees within the wall 8. The first control wires 9*a*, 9*b*, 9*c* are connected to the driving unit 2 at the proximal end of the wires 9*a*, 9*b*, 9*c*. The driving unit 2 induces pushing or pulling forces to move the control wires 9*a*, 9*b*, 9*c* by actuating those wires, and bends the bendable body 7 from the distal end 24. The second control wires 10*a*, 10*b*, 10*c* and third control wires, 11*a*, 11*b*, 11 *c* are similarly configured for their corresponding bendable segments 13 and 14, respectively.

Accordingly, by pushing and pulling the control wires 9*a* through 11*c* the first, the second and the third bendable segments 12, 13, 14, respectively, can individually bend the bendable medical device 3, in all three dimensions.

The subject bendable medical device 3 incorporates control wires 9, 10, 11, that can be fixed to the bendable body 7 by using minimal space in the bendable body wall 8. Because the anchors 21 are localized within the individual lumens 34, the bendable medical device 3 with the control wires 9, 10, 11, can be miniaturized effectively, especially when using multiple control wires 9, 10, 11. Additionally, the control wires 9, 10, 11, can be fully contained within the bendable body 7 wall 8, not needing to be outside the outer diameter 42 or inside the inner diameter 40; thus not impinging on the tool channel 18 or unnecessarily increasing the size of the medical device 3. By embedding the anchors 21 in the wall 8 of the bendable body 7, the control wires 9, 10, 11, can transmit pushing force, torque as well as pulling force to the bendable body 8. Therefore, the bendable medical device 3 can reduce the number of control wires 9, 10, 11, or force load per the control wire 9, 10, 11, to achieve the target bending maneuver in comparison to the conventional tendon-driven system with pulling forces.

Further depicted in FIGS. 6*a* through 6*c* are support wires 50 provided in the wall 8 of the bendable body 7. The support wires may provide added structural support to the wall 8 and may be anchored to the distal end 24 of a bending segments 12-14. The support wires 50 may run through lumens 34 configured in the wall 8, which may originate at the proximal part 19 of the bendable medical device 3. In certain embodiment, the support wires 50 may be configured for adjustable structural support of the wall 8. Exemplary adjustments for support may include employing various tensile strengths, configurations, resiliency of the support wires 50. In one embodiment, multiple support wires 50 may extend from the distal end 24 of the bendable medical device 3 to the proximal part 19 of the bendable medical device 3, thus allowing all segments 12-14 of the bendable body 7 to gain the kink prevention benefits.

Figure 7:
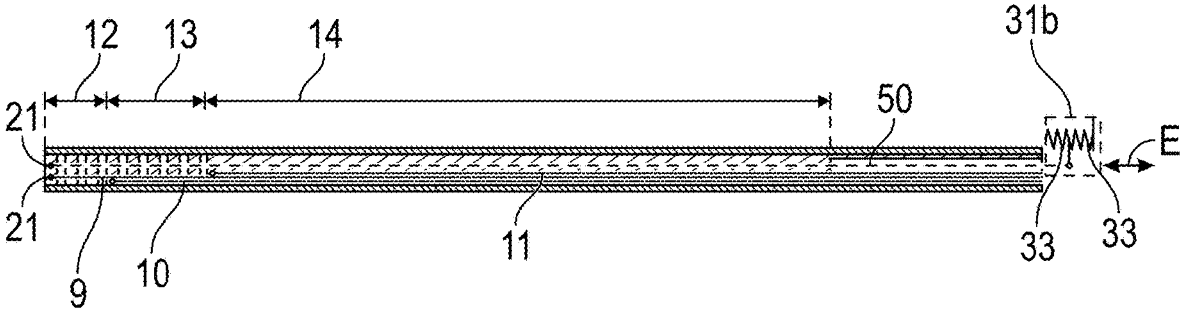
FIG. 7 illustrates a side perspective view of an exemplary bendable medical device, according to one or more embodiment of the subject apparatus, method or system.

FIGS. 5 and 7 provide side perspective views of exemplary bendable medical devices, according to one or more embodiment of the subject apparatus, method or system. FIG. 5 provides one example where the proximal end of the support wire 50 is attached to a proximal termination structure 31*a*. The proximal termination structure 31*a* is a slider element 32 that supports the support wire 50 slideably. Therefore, the support wire 50 would not be subjected to the tension and contraction forces when the bendable body 7 is bended, and minimize additional bending rigidity.

FIG. 7 is another embodiment, wherein a proximal termination structure 31*b* having a spring element 33. The support wires 50 are elastically terminated at the proximal termination structure 31*b*, and provide restoring force without increasing wall thickness.

Figure 8:
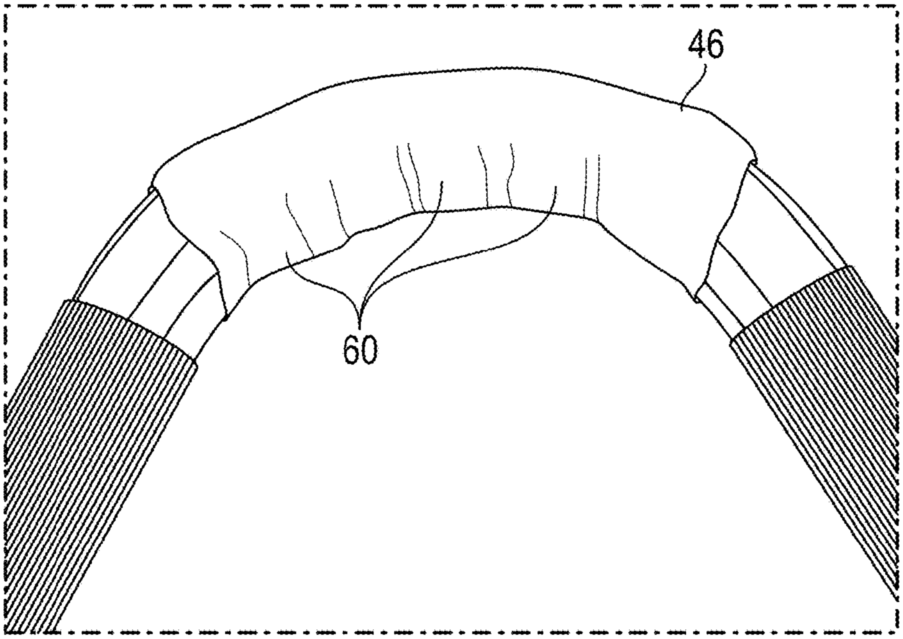
FIG. 8 provides a side perspective view of an exemplary medical device, in accordance with one or more embodiment of the subject apparatus, method or system.

FIG. 8 depicts an embodiment of the subject medical apparatus, wherein the bending section consists of cavities 30, which create evenly distributed wrinkles 60 in both the inner lining 44 and outer lining 46. Therefore, the cavities 30 avoid fatal kinking which may crush the tool channel 18 even when the bending sections have thin total wall thickness.

The entire catheter can move forwards/backwards, or may be rotated or manipulated otherwise for finite movement of the tip to reach the desired target. This can be performed manually or by driving the linear stage forwards/backwards.

Furthermore, the bending section can be expanded/compressed. In an embodiment, the bending section may comprise of material that can be stretchy, or cut in a fashion which can permit deformation (e.g. a skeleton structure). Deformation can be applied by moving all driving wires the same amount, applying heat, or filling chambers with a fluid.

A control software element may be integrated with the medical apparatus, wherein a user interface interacting with the control software can visually show the potential coverage area based on the current bend planes/angles of all bendable sections, as well as the capabilities of the most distal bendable section, which has been reserved for finite manipulation once the target has been reached.

This coverage area can be updated in real time as the shape of the medical apparatus and bending sections changes. An end user can fine tune the tip orientation and insertion depth before entering this target mode to ensure ideal initial alignment. The control software can present the end user with multiple options of depth/angles, and the end user can compare based on different properties (e.g. distance or coverage area/volume), and determine the most appropriate setting based on specific needs and other factors.

The control software can restrict bending to ensure the desired range is possible. By way of example, the end user can input a desired coverage area as one of the following: Percentage of lesion; A specific region within the lesion (or collection of); or size of circle, to name a few.

In various embodiments, the control software may calculate bending angles and/or trajectory, to situate the catheter in a position to allow for viewing and/or reaching two or more predetermined points in the subject, thus enabling the end user to view/reach all desired locations without having to further manipulate the medical apparatus. By way of example, the two or more points of interest may be of relative distance from each other, wherein the distal bending section would be able to reach the points of interest, as calculated by the control software.

During insertion of the medical apparatus, the control software can determine how the change to the shape will affect the coverage area, and therein calculate to limit the bending of the tip/middle section to ensure that translation in certain directions is not restricted. Furthermore, the control software may interact with the end user and notify the end user the desired ‘parking’ location of the bendable section (to switch into targeting mode) to ensure the region is fully reachable. Furthermore, the end user can also define an ideal ‘parking’ location based on the target location and degrees of freedom (wherein the degrees of freedom may be based on uncertainty), and the control software can determine the ideal combination of insertion depth and bend angles to ensure full coverage.

A controller can switch modes of the medical apparatus between a targeting mode (a first mode) and a leader following mode (a second mode). In the targeting mode, the controller controls a distal bending section (a first bending section) to bend in accordance with an instruction inputted by a user with a posture of the second bendable section maintained or held. In a leader following mode (a second mode), the controller directs the distal bending section to bend in accordance with an instruction inputted by the user and controls the proximal bending section to bend based on the bending amount of the distal bending section in a distance in which the bendable body is advanced after the distal bending section is bent. In the leader following mode, the proximal bending section is bent based on a bending amount of the distal bending section in a case where the bendable body is advanced and the second bending section reaches a position where the distal bending section is bent.

The end user can freely switch the controller between modes based on the end user’s desire/needs, or the modes may be switched automatically based on a position of tip of the catheter in the cavity. The tip position of the catheter can be acquired based on a detection by EM sensor. The controller is also capable of switching the modes between the targeting mode and the leader following mode when in another mode (for example, a parking mode).

The coverage area is calculated based on current shape/position of the catheter, which can be determined though one of the following: Forward kinematics of driving wires; Shape sensors along length of catheter (e.g. FBG); Position sensors embedded within catheter (e.g. EM); or other parameters deemed beneficial to determine coverage area.

The invention claimed is:

1. A medical apparatus comprising:

a bendable body having a proximal portion and a distal portion, the distal portion including a first bending section and a second bending section, with the first bending section in a position distal and next to the second bending section and the second bending section in a position distal to the proximal portion, the first bending section including: at least two guide rings disposed in the bendable body and spaced a distance from one another to create a cavity, a tip, and a wall extending a length of the first bending section and operating to encapsulate the at least two guide rings, wherein the wall comprises a resilient outer lining and a resilient inner lining for encapsulating the at least two guide rings;

a first control wire running through the proximal portion and the second bending section and being connected to a distal end of the first bending section;

a second control wire running through the proximal portion and being connected to a distal end of the second bending section;

at least two lumens in the bendable body extending a length of the bendable body through the first bending section and the second bending section;

an actuator attached to a proximal end of the first control wire and to a proximal end of the second control wire, wherein the actuator operates to actuate the first control wire and the second control wire independently; and a controller or processor that operates to:

select one of, or switch between, a plurality of modes;

in a case where the controller or processor has selected or switched to a targeting mode of the plurality of modes, control the first control wire and/or the second control wire, via the actuator, to bend the first bending section and/or the second bending section such that the first bending section and the second bending section operate to be manipulated by actuation of the first control wire and the second control wire, respectively, while manipulating the proximal portion so that: (i) the first bending section and the second bending section operate to bend or to be moved or oriented while a posture of the proximal portion is not moved by the controller or processor, (ii) the second bending section is disposed or positioned at or near a location to reach or be near a target, sample, or object, and (iii) the first bending section operates to be manipulated in any direction to reach the target, sample, or object without moving the second control wire after the second bending section has reached or is disposed at or near the location or near the target, sample, or object; and in a case where the controller or processor has selected or switched to a follow a leader mode of the plurality of modes, control the first bending section to bend automatically or in accordance with an instruction received from or input by a user of the medical apparatus, and control the second bending section to bend based on:

(i) a bending amount of the first bending section in a distance in which the bendable body is advanced after the first bending section is bent, and/or (ii) a bending amount of the first bending section in a case where the bendable body is advanced and the second bending section reaches a position where the first bending section was bent over a distance or along a path, wherein a coverage area for the first bending section of the distal portion or for the bendable body, based on the location and bending planes/angles of the second bending section of the distal portion or of the bendable body is shown on a display, and the controller or processor further operates to: (i) ensure a desired coverage area to reach and/or view the target, sample, or object, and (ii) calculate bending angles and trajectory to situate the medical apparatus in a position to allow for viewing and/or reaching of two or more predetermined points in the target, sample, or object without having to further move one of the proximal portion, the first bending section of the distal portion, and/or the second bending section of the distal portion, where the target, sample, or object is a lesion and the coverage area includes the two or more predetermined points in the lesion.

2. The apparatus of claim 1, wherein the manipulation of the first bending section is accomplished while the second bending section is stationary.

3. The apparatus of claim 1, wherein the manipulation of the first bending section is one or more of the following: rotation, fore and aft travel, panning, translation, movement in two axes, and/or movement in three axes.

4. The apparatus of claim 1, wherein the at least two guide rings are attached to at least a portion of the wall.

5. The apparatus of claim 1, wherein the resilient inner lining defines a hollow chamber.

6. The apparatus of claim 1, further comprising a support wire slideably situated in one of the at least two lumens.

7. The apparatus of claim 1, wherein the at least two lumens extend through the at least two guide rings.

8. The apparatus of claim 1, further comprising:

a third bending section proximal to both the first bending section and the second bending section, the third bending section being proximally next to the second bending section and the third bending section being in a position distal and next to the proximal portion; and a third control wire running through the proximal portion and being connected to a distal end of the third bending section, wherein the at least two lumens further extend through the third bending section, and wherein the actuator is attached to a proximal end of the third control wire, and the actuator further operates to actuate the first control wire, the second control wire, and the third control wire independently.

9. The apparatus of claim 1, wherein the first control wire and the at least two lumens comprise or include a radio opaque material.

10. The apparatus of claim 1, wherein the controller or processor further operates to:

calculate a path of the bendable body.

11. The apparatus of claim 1, wherein the controller or processor further operates to one or more of the following:

switch between two or more of the plurality of modes, where the two or more of the plurality of modes includes at least the targeting mode and the follow the leader mode, or the plurality of modes includes at least the targeting mode, the follow the leader mode, and/or a different mode or a parking mode; and/or switch to a parking mode of the plurality of modes, where controller or processor further operates to control the medical apparatus to be disposed at a set or predetermined parking location based on a target location and/or degrees of freedom to ensure that the coverage area is reachable or targetable.

12. The apparatus of claim 1, wherein the controller or processor further operates to one or more of the following:

translate a position of the tip of the first bending section in space without affecting an orientation of the tip of the first bending section and/or without affecting a position of the medical apparatus; and/or translate a position of the tip of the first bending section in space such that a set or predetermined, finite adjustment of a location or locations in the target, sample, or object is achieved and/or such that an increase in surface area coverage for the target, sample, or object is achieved compared to a case where the position of the tip of the first bending section is not translated.

13. The apparatus of claim 1, wherein the controller or processor further operates to one or more of the following:

(i) deform the first bending section and/or the second bending section to expand or compress the first bending section and/or the second bending section to increase a maneuverability or freedom of the bendable body while disposed in the target, sample, or object;

(ii) deform the first bending section and/or the second bending section, via the actuator, by expanding or compressing a flexible material of the first bending section and/or the second bending section;

(iii) deform the first bending section and/or the second bending section, via the actuator, by expanding or compressing a skeletal structure of the first bending section and/or the second bending section; and/or (iv) deform the first bending section and/or the second bending section by moving all driving wires a set or predetermined amount, via the actuator.

14. The apparatus of claim 1, further comprising wherein the tip or a distal end of the bendable body further includes a tool channel, the tool channel operating to include an orientation feature or structure and to include a camera that is detachably attached with or in the tool channel.

15. An apparatus comprising:

a bendable body including at least a distal bending section and a proximal bending section, the distal bending section being disposed next to the proximal bending section; and a controller or processor that operates to:

control the distal bending section to bend and control the proximal bending section to bend, select one of, or switch between, a plurality of modes, in a case where the controller or processor has selected or switched to a first mode of the plurality of modes, control the distal bending section to bend automatically or in accordance with an instruction inputted by a user so that (i) the distal bending section bends or is moved or oriented while the controller or processor does not bend or change a posture of the proximal bending section, (ii) the proximal bending section is disposed or positioned at or near a location to reach or be near a target, sample, or object, and (iii) the distal bending section operates to be manipulated to reach the target, sample, or object after the proximal bending section has reached or is disposed at or near the location or near the target, sample, or object, and in a case where the controller or processor has selected or switched to a second mode, control the distal bending section to bend automatically or in accordance with an instruction inputted by a user of the apparatus, and control the proximal bending section to bend based on:

(i) a bending amount of the distal bending section in a distance in which the bendable body is advanced after the distal bending section is bent, and/or (ii) a bending amount of the distal bending section in a case where the bendable body is advanced and the proximal bending section reaches a position where the distal bending section was bent over a distance or along a path, wherein translation of a tip of the distal bending section is accomplished by manipulating the proximal bending section in the second mode, and the second mode is a follow the leader mode, and wherein a coverage area for the distal bending section or for the bendable body, based on the location and bending planes/angles of the proximal bending section or of the bendable body is shown on a display, and the controller or processor further operates to: (i) ensure a desired coverage area to reach and/or view the target, sample, or object, and (ii) calculate bending angles and trajectory to situate the apparatus in a position to allow for viewing and/or reaching of two or more predetermined points in the target, sample, or object without having to further move one of the proximal bending section and/or the distal bending section, where the target, sample, or object is a lesion and the coverage area includes the two or more predetermined points in the lesion.

* * * * *